(12) United States Patent
Smith et al.

(10) Patent No.: US 10,105,534 B2
(45) Date of Patent: Oct. 23, 2018

(54) CARDIAC LEAD WITH HELIX SUTURE SLEEVE

(71) Applicant: PACESETTER, INC., Sylmar, CA (US)

(72) Inventors: Tyler Smith, Mission Hills, CA (US); Matthew Malone, Valencia, CA (US)

(73) Assignee: PACESETTER, INC., Sylmar, CA (US)

( * ) Notice: Subject to any disclaimer, the term of this patent is extended or adjusted under 35 U.S.C. 154(b) by 183 days.

(21) Appl. No.: 15/057,652

(22) Filed: Mar. 1, 2016

(65) Prior Publication Data

US 2017/0252554 A1    Sep. 7, 2017

(51) Int. Cl.
    *A61N 1/05*    (2006.01)
(52) U.S. Cl.
    CPC ...... *A61N 1/057* (2013.01); *A61N 2001/0582* (2013.01)

(58) Field of Classification Search
    CPC .................. A61N 1/057; A61N 2001/0582
    See application file for complete search history.

(56) References Cited

U.S. PATENT DOCUMENTS

2011/0009935 A1*    1/2011    Kane .................. A61N 1/05
                                                 607/116

\* cited by examiner

*Primary Examiner* — Rex R Holmes

(57) ABSTRACT

An implantable therapy lead is disclosed herein. In one embodiment, the therapy lead includes an elongated lead body and a suture sleeve. The elongated lead body has a proximal region and a distal region opposite the proximal region. The suture sleeve is supported on the lead body and has a proximal end, a distal end opposite the proximal end, an outer surface extending between the proximal end and distal end, and an inner surface radially inward of the outer surface and extending between the proximal end and distal end. The inner surface defines a lumen through which the elongated lead body extends. A helical structure helically extends about a longitudinal center axis of the lumen and along the inner surface.

16 Claims, 7 Drawing Sheets

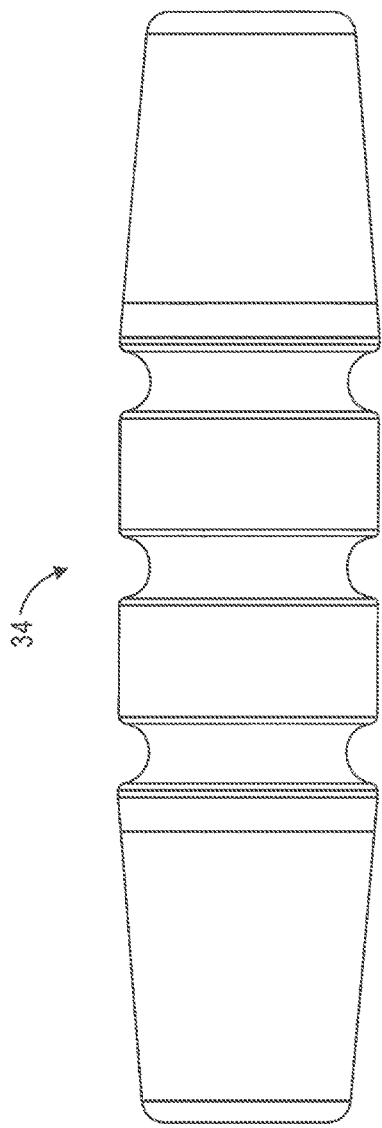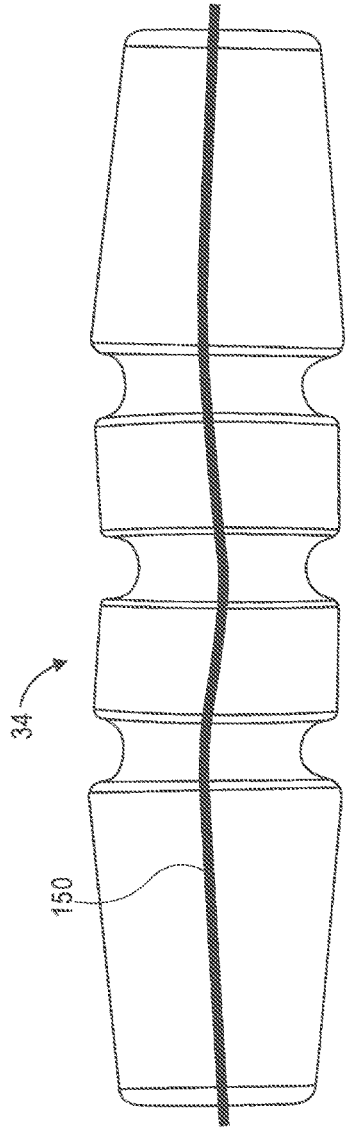

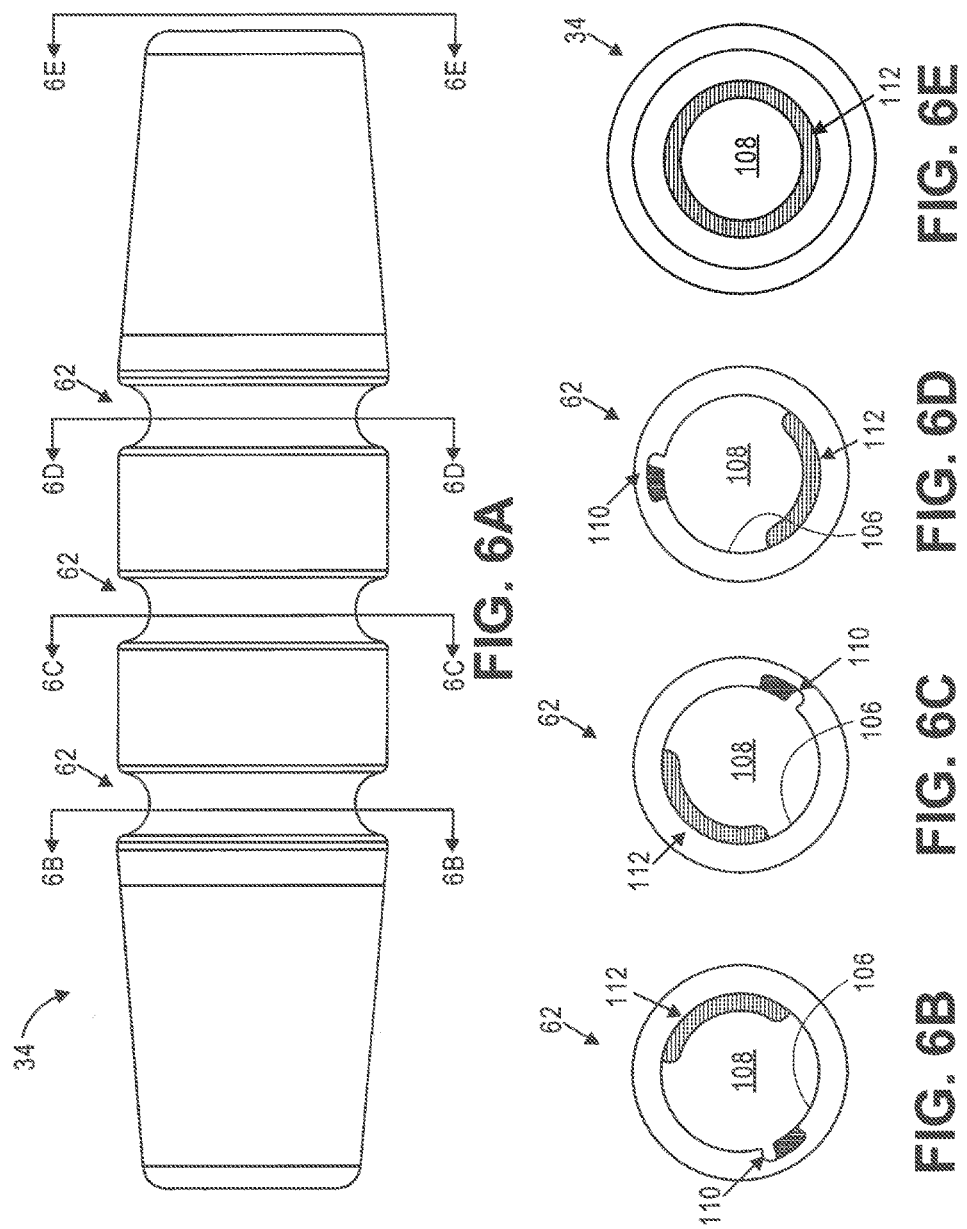

CARDIAC LEAD WITH HELIX SUTURE SLEEVE

FIELD OF THE INVENTION

The present invention relates to medical apparatus and methods. More specifically, the present invention relates to implantable therapy leads and methods of assembling such leads.

BACKGROUND OF THE INVENTION

An implantable cardiac pulse generator (e.g., pacemaker, implantable cardioverter defibrillator (ICD), or etc.) is typically electrically coupled to therapy locations in the heart via elongated implantable cardiac leads that can be advanced into the patient's heart. The leads include electrodes to sense electrical activity and deliver therapeutic stimulation to heart tissue A suture sleeve is supported on the elongated body of each lead and subcutaneously fixates the lead to body tissue. By anchoring the lead to the patients' body, movement of the lead body can be mitigated thus reducing the prevalence of dislodgements.

In some instances, suture sleeves have been known to slide after being sutured to the body tissue. To help reduce the possibility of slippage, physicians have been known to apply excessive tie-down force to the sutures and, as a result, end up damaging the lead, thereby resulting in electrical noise. Also, in order to re-position the suture sleeve, the suture must be clipped and re-tied which presents an opportunity to damage the lead body from re-tying of the suture as well as potentially clipping the lead outer tubing during removal.

Numerous solutions have been created to address these suture sleeve issues, but none have proven to be cost effective. Accordingly, there is a need in the art for an improved suture sleeve and related methods of use and manufacture.

SUMMARY

An implantable therapy lead is disclosed herein. In one embodiment, the therapy lead includes an elongated lead body and a suture sleeve. The elongated lead body includes a proximal region and a distal region opposite the proximal region. The suture sleeve is supported on the lead body and includes a proximal end, a distal end opposite the proximal end, an outer surface extending between the proximal end and distal end, and an inner surface radially inward of the outer surface and extending between the proximal end and distal end. The inner surface defines a lumen through which the elongated lead body extends. A helical structure helically extends about a longitudinal center axis of the lumen and along the inner surface.

In one version of the embodiment, the helical structure includes a helical recess defined in the inner surface and projecting radially outward from inner surface. In one version of the embodiment, the helical structure includes a helical protrusion extending along the inner surface and projecting radially inward from inner surface. In one version of the embodiment, the helical structure can include both the helical recess and the helical protrusion.

In one embodiment, the therapy lead includes an elongated lead body and a suture sleeve. The elongated lead body includes a proximal region and a distal region opposite the proximal region. The suture sleeve is supported on the lead body and includes a proximal end, a distal end opposite the proximal end, an outer surface extending between the proximal end and distal end, an inner surface radially inward of the outer surface and extending between the proximal end and distal end, and a structure. The inner surface defines a lumen through which the elongated lead body extends. The structure at least one of projects radially inward from the inner surface or projecting radially outward from the inner surface.

In one version of the embodiment, the structure projects radially inward from the inner surface and includes a protrusion, and this protrusion can include a helical aspect. In one version of the embodiment, the structure projects radially outward from the inner surface and includes a recess defined in the inner surface, and this recess can include a helical aspect. In one version of the embodiment, the helical structure includes both the recess and the protrusion, and one or more of these may be helical or not.

While multiple embodiments are disclosed, still other embodiments of the present invention will become apparent to those skilled in the art from the following detailed description, which shows and describes illustrative embodiments of the invention. As will be realized, the invention is capable of modifications in various aspects, all without departing from the spirit and scope of the present invention. Accordingly, the drawings and detailed description are to be regarded as illustrative in nature and not restrictive.

BRIEF DESCRIPTION OF THE DRAWINGS

FIGS. 5A and 5B are, respectively, a longitudinal side view of the suture sleeve depicting its appearance in an untied state and the same side view of the suture sleeve except depicting its appearance in tied state.

FIG. 6A is a longitudinal side view of the suture sleeve.

FIGS. 6B-6D are, respectively, transverse cross sections of the suture sleeve taken along each of the three circumferential recesses at section lines 6B-6B, 6C-6C and 6D-6D in FIG. 6A.

FIG. 6E is an end elevation view of the suture sleeve as taken along line 6E-6E in FIG. 6A.

DETAILED DESCRIPTION

Figure 1:
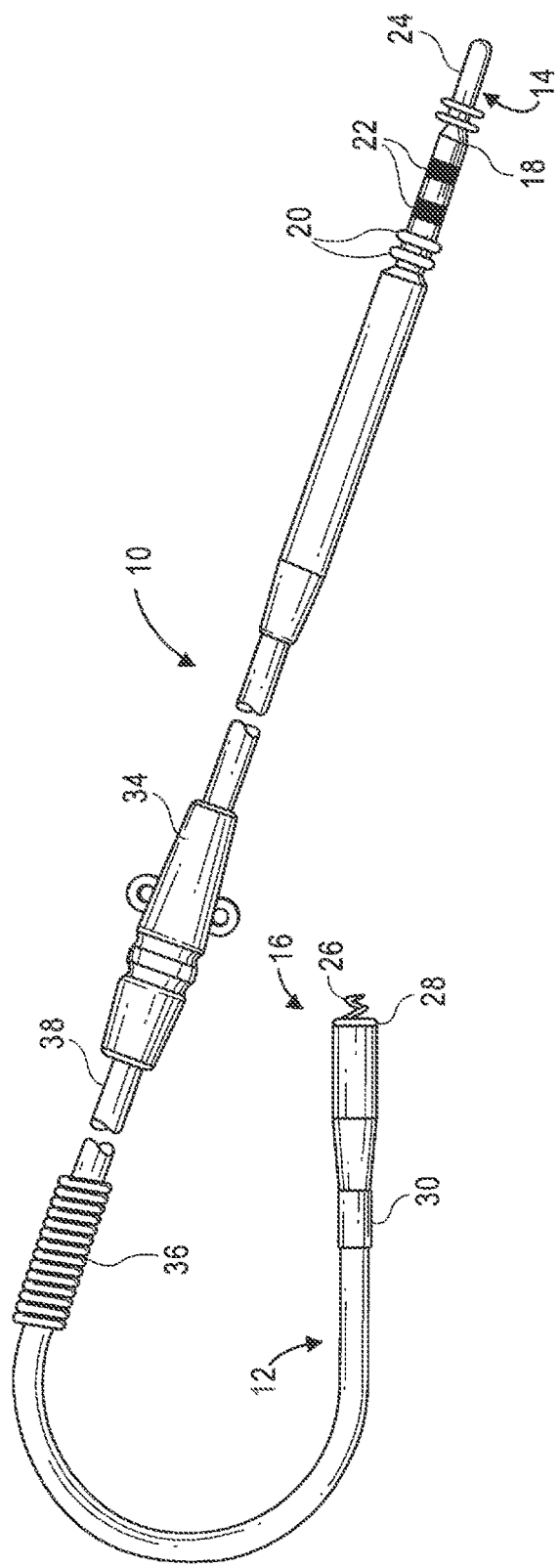
FIG. 1 is a plan view of an embodiment of a lead, wherein an active fixation anchor of the lead is shown in an extended or deployed state.

Implantable therapy leads 10 (e.g., a CRT lead, etc.) and methods of using and manufacturing such leads are disclosed herein. In one embodiment, the therapy lead 10 includes a suture sleeve 34 supported on the elongated body 12 of the lead. The suture sleeve 34 includes helical features 110, 112 defined in the interior surface 106 that defines the lumen 108 of the suture sleeve and through which the lead body 12 extends.

When the suture sleeve is sutured to the lead body, the helical internal features 110, 112 of the suture sleeve 34 gently manipulate the lead body 12 into a corkscrew shape. The helical contouring shape changes the way the forces are distributed along the lead body, affectively increasing the resistance to slipping between the suture sleeve and the lead body.

In an untied condition, the helical internal features 110, 112 also allow for the suture sleeve 34 to be repositioned easily along the lead body 12, the resistance to slipping of the helical internal features only manifesting itself when the suture sleeve is sutured. This suture induced resistance to slipping of the helical features of the suture sleeve is advantageous as a suture sleeve in the untied condition should ideally slide easily along the lead body.

The helical internal features 110, 112 of the suture sleeve 34 may be in the form of a helical trough or recess 110 and a helical ridge or protrusion 112, both of which are measured against the rest of the inner circumferential surface 106 of the lumen 108 of the suture sleeve 34. The two helical features 110, 112 may have the same general helical pitch and a generally constant offset. The helical recess 110 acts as a window-like feature to allow the silicone (or similar material forming the suture sleeve 34) to deform and maintain grip along the lead body. Without such a window-like feature 110, when the silicone is constricted by the suture tie, it will form into an oval-like shape and not circumferentially grip the lead body 12. The window-like feature 110 acts as a space for the silicone to move into and help the silicone contact the lead body 12 uniformly.

a. Overview of Lead

To begin a detailed discussion of the lead 10, reference is made to FIG. 1, which is a plan view of an embodiment of the lead 10. While the following overview of the lead is given in the context of an active fixation lead, the teachings herein are equally applicable to passive fixation leads, and the present disclosure should not be limited to active fixation leads. Instead, the present disclosure should be interpreted as encompassing implantable leads of all types and of all fixation mechanisms, including passive fixation mechanisms in addition to active fixation mechanisms.

As can be understood from FIG. 1, in one embodiment, the lead 10 is designed for intravenous insertion and contact with the endocardium, and as such, may be conventionally referred to as an endocardial lead. In other embodiments, the lead 10 may be of other configurations for other implantation types, such as, for example, leads implanted in the intrapericardial space.

As indicated in FIG. 1, the lead 10 is provided with an elongated lead body 12 that extends between a proximal region 14 and distal region 16 of the lead 10. The proximal region 14 of the lead 10 includes a connector assembly 18, which is provided with sealing rings 20 and carries at least one or more electrical connectors in the form of ring contacts 22 and a pin contact 24. The connector assembly 18 is configured to be plugged into a receptacle of a pulse generator, the sealing rings 20 forming a fluid-tight seal to prevent the ingress of fluids into the receptacle of the pulse generator. When the connector assembly 18 is plugged into the pulse generator receptacle, the contacts 22, 24 electrically connect with the circuitry of the pulse generator such that electrical signals can be administered and sensed by the pulse generator via the electrical pathways of the lead 10.

The connector assembly 28 is constructed using known techniques and is preferably fabricated of silicone rubber, polyurethane, silicone-rubber-polyurethane-copolymer ("SPC"), or other suitable polymer. The electrical contacts 22, 24 are preferably fabricated of stainless steel or other suitable electrically conductive material that is biocompatible.

As shown in FIG. 1, the distal region 16 of the lead 20 includes the helical active fixation anchor 26 distally extending from an extreme distal tip end 28 of the lead 20 when the active fixation anchor 26 is in a deployed state. The anchor 26 may be transitioned to a non-deployed state via retraction of the anchor 26 into the confines of the distal region 16 of the lead 10 or by an obturator or other structural member being combined with the anchor 26 to inhibit the anchor 26 from being able to penetrate tissue.

In one embodiment, the anchor 26 is deployed or placed in the extended state by rotating the contact pin 24, which is coupled via a helical conductor to the anchor 26. As the contact pin 24 is rotated about its longitudinal axis, the helical conductor and sharp helical anchor 26 rotate relative to the rest of the lead 10 to cause the anchor 26 to extend from the lead distal end 28 to screw into myocardial tissue. In some other embodiments, a stylet or other tool is inserted through the lead body 12 to deploy the anchor 26 via rotation and/or sliding distal displacement of the anchor 26 brought about by complementary interaction of the stylet or other tool with structural features of, or associated with, the anchor 26.

The anchor 26 may also be configured to act as an electrode in addition to providing active fixation to heart tissue. Where the anchor 26 is also configured to act as an electrode, depending on the dictates of the pulse generator, the anchor 26 may be employed for sensing electrical energy and/or administration of electrical energy (e.g., pacing). The anchor 26 is electrically coupled to the pin contact 24 of the connector assembly 18 via the electrical conductor extending through the lead body 12 and the connector assembly 18, Depending on the embodiment, the electrical conductor may be in the form of helically coned electrical conductors. In other embodiments, the conductor may be in the form of wires, cables or other electrical conductors that are linear or helically coiled in configuration.

The distal region 16 of the lead 10 also includes an annular ring electrode 30 proximally offset from the extreme distal tip end 28 of the lead 10. Depending on the dictates of the pulse generator, this ring electrode 30 may be employed for sensing electrical energy and/or administration of electrical energy (e.g., pacing). The ring electrode 30 is electrically coupled to one of the ring contacts 22 of the connector assembly 18 via another electrical conductor extending through the lead body 12 and the connector assembly 18. This electrical conductor may also be in the form of helically coded electrical conductors. In other embodiments, this conductor may be in the form of wires, cables or other electrical conductors that are linear or helically coiled in configuration.

As indicated in FIG. 1, the lead 10 may include a fixation or suture sleeve 34 slidably mounted around the lead body 12. The suture sleeve 34 serves to stabilize the pacing lead 10 at the site of venous insertion.

Where the lead 10 is equipped for defibrillation, a shock coil 36 will be supported on the lead body 12 proximal the ring electrode 30 and distal the fixation sleeve 34. The shock coil 36 is electrically coupled to one of the ring contacts 22 of the connector assembly 18 via electrical conductors extending through the lead body 12 in the form of wires, cables or other electrical conductors that are linear or helically coiled in configuration.

The lead body 12 includes an outer insulation sheath 38 and an inner insulation sheath. The outer insulation sheath 38 is preferably fabricated of silicone rubber, polyurethane, silicone rubber-polyurethane-copolymer (SPC), or other suitable polymer. The inner insulation sheath may be formed of the same material as the outer insulation sheath 39 or from another material such as, for example, polytetrafluoroethylene ("PTFE"). The insulation sheaths isolate the interior components of the lead 10, including the electrical conductors from each other. The outer insulation sheath 38 isolates the inner components of the lead 10 from the surrounding environment and may be single or multi-layer construction.

The lead body 12 may be constructed to include a hollow interior extending from the proximal region 14 to the distal region 16. The hollow interior allows for the introduction of a stylet, guidewire or other device during implant, which is beneficial in allowing the surgeon to guide the otherwise flexible lead 10 from the point of venous insertion to the myocardium.

b. The Helix Suture Sleeve

Figure 2:
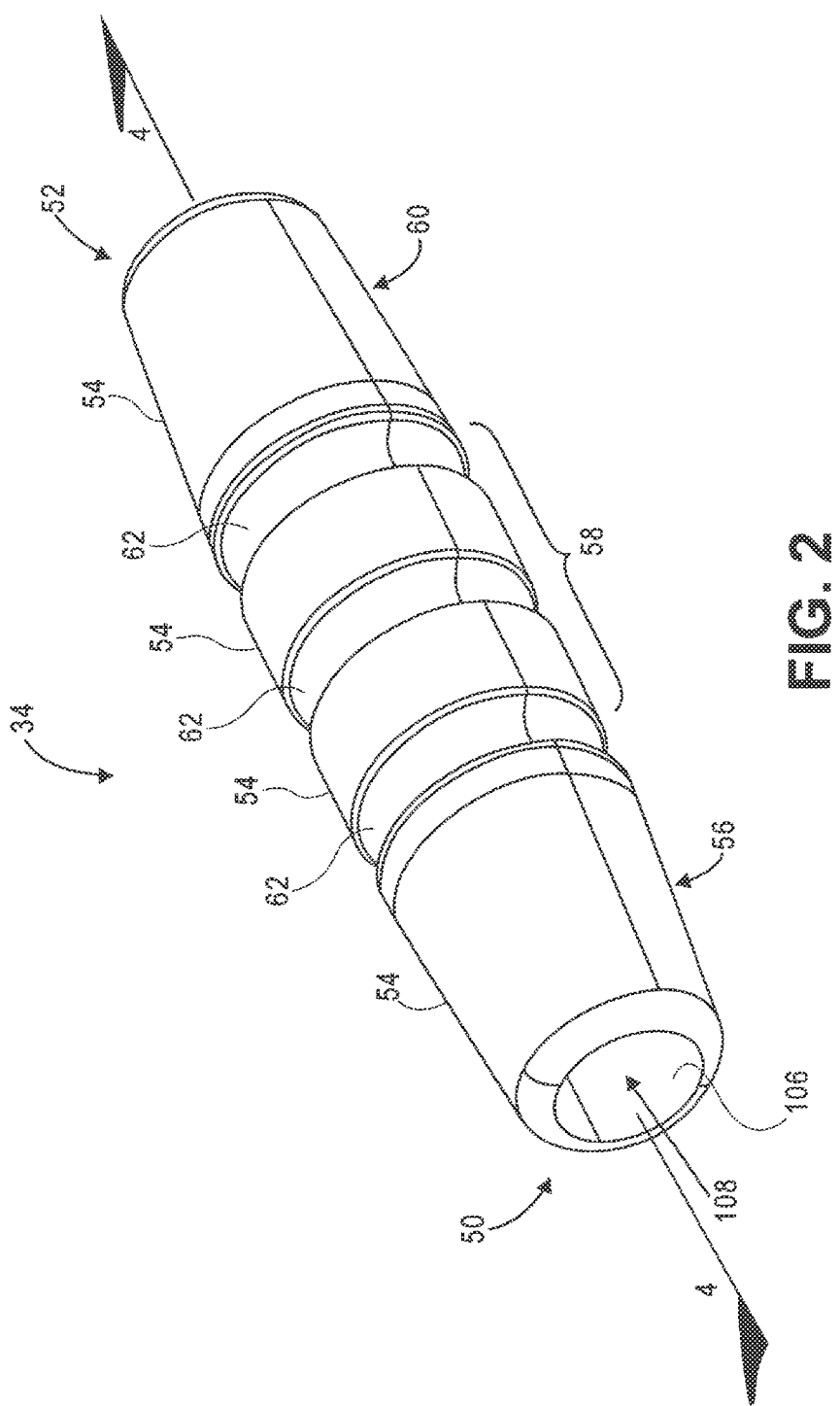
FIG. 2 is an isometric view of an embodiment of a suture sleeve capable of being employed on a lead similar to that depicted in FIG. 1.
Figure 3:
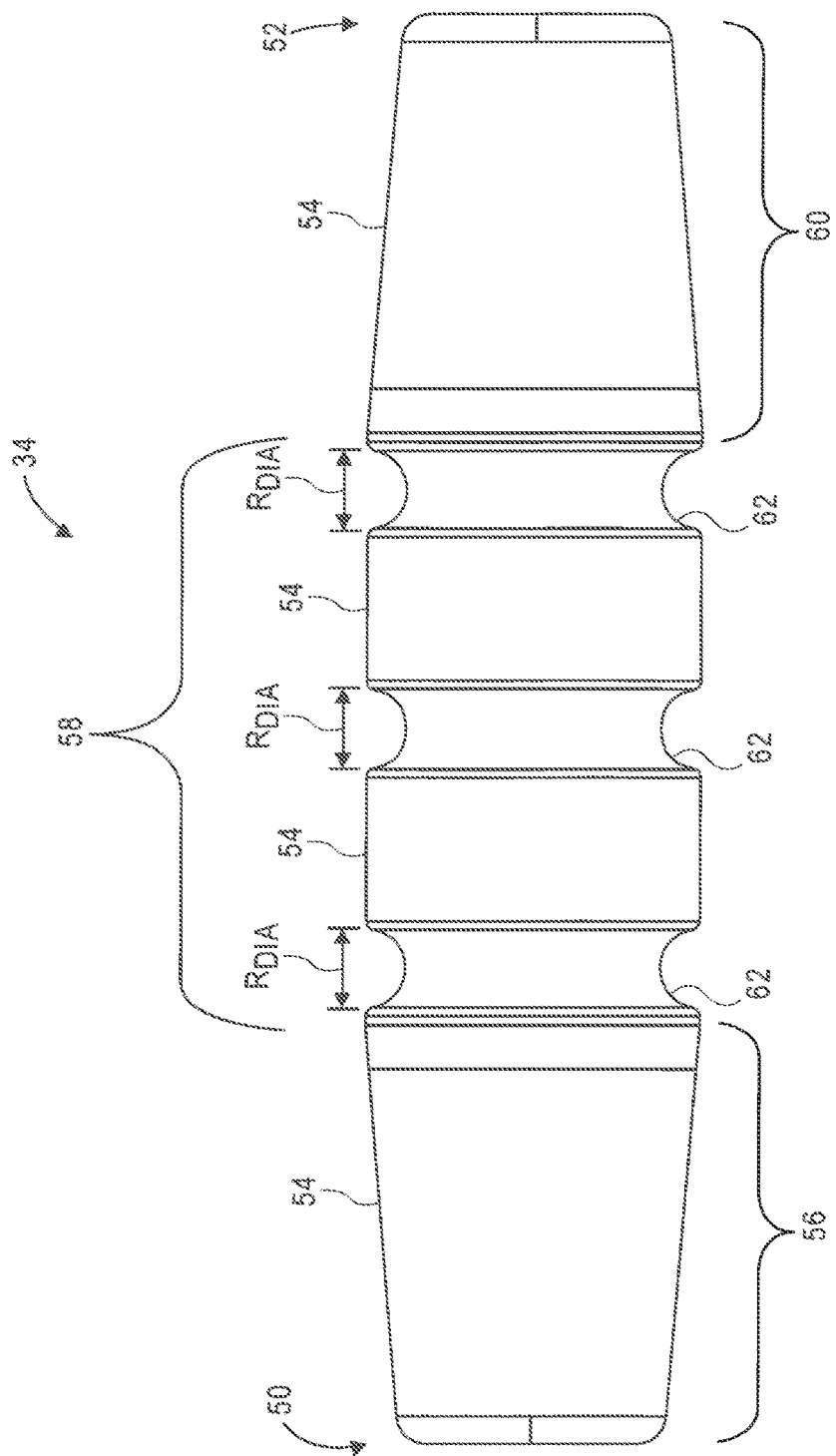
FIG. 3 is a longitudinal side view of the suture sleeve.

FIG. 2 is an isometric view of an embodiment of a suture sleeve 34 capable of being employed on a lead 10 similar to that depicted in FIG. 1, and FIG. 3 is a longitudinal side view of the suture sleeve. As shown in FIGS. 2 and 3, the sleeve 34 includes a proximal end 50, a distal end 52 opposite the proximal end, and an outer surface 54 extending between the proximal end and distal end. The outer surface 54 has a proximal conical region 56, a cylindrical middle region 58, and a distal conical region 60. The cylindrical middle region 58 includes one or more circumferential troughs or recesses 62 defined in the outer surface 54 and projecting radially inward from the outer surface. For example, in one embodiment, the cylindrical middle region 58 includes three circumferential recesses 62 evenly spaced apart from each other along the length of the cylindrical middle region 58. In other embodiments, there may be a greater or lesser number of circumferential recesses 62 along the length of the cylindrical middle region 58.

As can be understood from FIGS. 2 and 3, in one embodiment, each circumferential recess 62 has a semi-circular transverse cross section with a recess diameter $R_{DIA}$ of between approximately 0.15 inches and approximately 0.24 inches. While the circumferential recess 62 is shown as having a semi-circular cross section in FIGS. 2 and 3, in other embodiments, the transverse cross section of the circumferential recess 62 may be triangular, rectangular, semi-elliptical, or etc.

Figure 4:
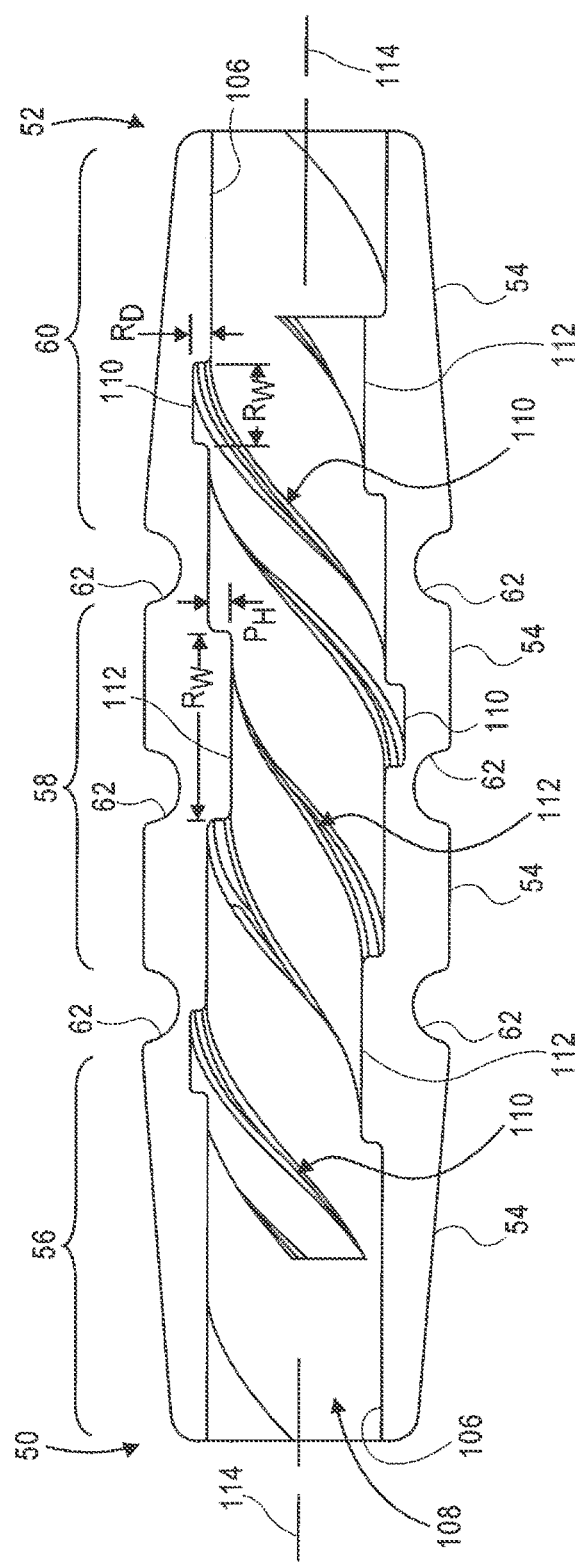
FIG. 4 is a longitudinal cross section of the suture sleeve taken along section line 4-4 in FIG. 2.

FIG. 4 is a longitudinal cross section of the suture sleeve 34 taken along section line 4-4 in FIG. 2. As can be understood from FIG. 4, the sleeve 34 also includes an inner surface 106 radially inward of the outer surface 54. The inner surface extends between the proximal end 50 and distal end 52. The inner surface 106 defines a lumen 108 through which the elongated lead body 12 extends, as indicated in FIG. 1. The inner surface 106 is at least substantially if not completely cylindrical.

As shown in FIG. 4, the suture sleeve 34 also includes one or more helical structures 110, 112 helically extending about a longitudinal center axis 114 of the lumen 108 and along the inner surface 106. One of the helical structures may be in the form of a helical recess 110 defined in the inner surface 106 and projecting radially outward from inner surface.

In one embodiment, the helical trough or recess 110 includes a rectangular transverse cross section having a recess depth $R_D$ of between approximately 0.008 inches and approximately 0.012 inches relative to the inner surface 106 and a transverse recess width $R_W$ of between approximately 0.04 inches and approximately 0.05 inches. While the helical recess 110 is shown as having a rectangular transverse cross section in FIG. 4, in other embodiments, the transverse cross section of the helical recess may be triangular, semi-circular, semi-elliptical, or etc.

As illustrated hi FIG. 4, the other of the helical structures may be in the form of a helical ridge or protrusion 112 projecting radially inward from the inner surface 106. In one embodiment, the helical protrusion 112 includes a rectangular transverse cross section having a protrusion height $P_H$ of between approximately 0.008 inches and approximately 0.016 inches relative to the inner surface 106 and a transverse protrusion width $P_W$ of between approximately 0.09 inches and approximately 0.11 inches. While the helical protrusion 112 is shown as having a rectangular transverse cross section in FIG. 4, in other embodiments, the transverse cross section of the helical recess may be triangular, semi-circular, semi-elliptical, or etc.

The pitch of the helical recess 110 may be between approximately 7 threads per inch and approximately 11 threads per inch, and the pitch of the helical protrusion 112 may be between approximately 7 threads per inch and approximately 11 threads per inch. The pitches of the helical recess and helical protrusion may be the same, or may be different but not so different that the helical recess and helical protrusion intersect.

As indicated in FIG. 4, the helical recess 110 and the helical protrusion 112 are helically staggered or offset relative to each other. In one embodiment, the offset spacing between immediately adjacent turns of the helical recess and helical protrusion are equal, while in other embodiments, the offset spacing may be different.

As can be understood from FIG. 4, the helical recess 110 and the helical protrusion 112 have different transverse widths. For example, in one embodiment and as illustrated in FIG. 4, the helical protrusion 112 has a transverse width $P_W$ that is wider than the transverse width $R_W$ of the helical recess 110. In other embodiments, the transverse width of the helical protrusion may be equal to or smaller than the transverse width of the helical recess.

In one embodiment, as shown in FIG. 4, the transverse widths, height and depth of the helical recess and helical protrusion may be constant along their respective helical lengths. In other embodiments, any one or more of the transverse widths, height or depth of the helical recess and helical protrusion may vary along their helical lengths.

As can be understood from FIG. 4, in one embodiment, the helical structures 110, 112 and the circumferential recesses 62 overlap each other along at least one location along a distal-proximal length of the suture sleeve 34 and, more specifically in one embodiment, along the vast majority of their common distal-proximal extents.

FIGS. 5A and 5B are, respectively, a longitudinal side view of the suture sleeve 34 depicting its appearance in an untied state and the same side view of the suture sleeve 34 except depicting its appearance in tied state. As indicated in FIG. 5A, when the suture sleeve is in the untied state, the suture sleeve is straight (i.e., not deflected) and symmetrical about its longitudinal center axis. In contrast, on account of its internal helical structures, when the suture sleeve is in the tied state, the suture sleeve is not straight (i.e., it is deflected) and it is not symmetrical about its longitudinal center axis, as can be understood from the finite element analysis line 150 extending the length of the suture sleeve 34 in FIG. 5B. Specifically, the internal helical structures 110, 112 create material offsets, which when acted on by the constrictive forces of the sutures used to tie down the suture sleeve 34 on the lead body 12, create an undulating shape inside the suture sleeve to slightly bend or undulate the lead body and increase friction between the interior of the suture sleeve and lead body.

As can be understood from FIGS. 6A-6E, which are, respectively, a longitudinal side view of the suture sleeve 34, transverse cross sections taken along each of the three circumferential recesses 62 at section lines 6B-6B, 6C-6C and 6D-6D, and an end elevation view as taken along line 6E-6E, the helical recess 110 and the helical protrusion 112 are opposite each other at each circumferential recess 62 and helically rotate about the inner circumferential surface 106 of the lumen 108 approximately 120 degrees from circumferential recess 62 to immediately adjacent circumferential recess 62. These three transverse cross sections of FIGS. 6B-6D illustrate the unequal distribution of mass of the suture sleeve within the lumen of the suture sleeve on account of the helical features. The helical configuration and it unequal mass distribution work to force the suture sleeve 34 to bend in a three-dimensional corkscrew shape when an exterior force is compressed about the suture sleeve at these exterior circumferential recesses 62 such as, for example, by sutures tying the suture sleeve to the lead body.

Displacing a lead body through a convoluted shape, such as that depicted in FIG. 5B, is much more difficult than a cylindrical conduit. The frictional values are increased as a result of increased normal values. As the lead body moves through a bend, the normal values along the bend are greatly increased, thus increasing the friction and deformation of the lead body through the bend. This tortuosity is induced when the circumferential recesses 62 are tied, and this tortuosity is shown via the finite element line 150 of FIG. 5B.

Figure 7:
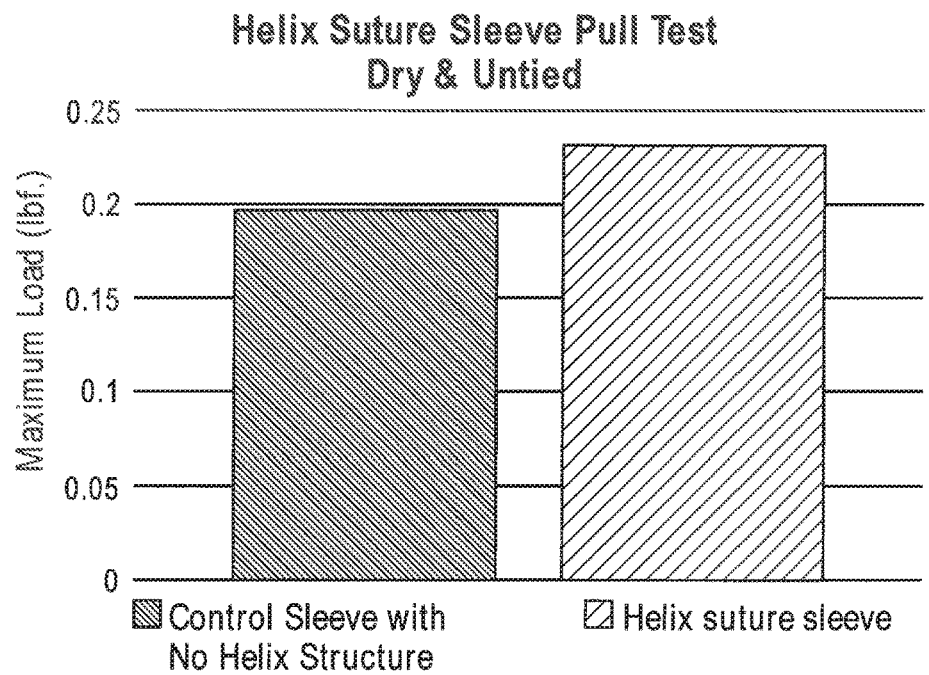
FIG. 7 is a graph depicting comparison dry untied pull test results for a control sleeve having no helix structure and being identical to a suture sleeve used in the industry and the helical structure equipped suture sleeve depicted in FIGS. 2-6E.

FIG. 7 is a graph depicting comparison dry untied pull test results for a control sleeve having no helix structure and being identical to a suture sleeve used in the industry and the new helical structure equipped suture sleeve 34 depicted in FIGS. 2-6E. The untied test is of interest as it shows that a physician can quickly and easily position the suture sleeve to the desired location if the pull force is not too large or too small. For example, in one embodiment, a desirable sleeve maximum pull force on an untied and dry suture sleeve is 0.25 lbf, while a pull force that is too small means the suture sleeve will slide when the lead is held in a vertical orientation.

As can be understood from a comparison of the untied pull force results of FIG. 7, the helical design is statistically identical (P<0.05) with respect to the dry untied pull force needed to position along the lead while also staying stationary when held in the vertical position. This amount of pull force also allows useful relative testing because the "preload" on the suture sleeve prior to tie-down is the same. With this in mind, any differences noted in the pull strength of the wet and tied tests will be indicative of the variable changed.

Figure 8:
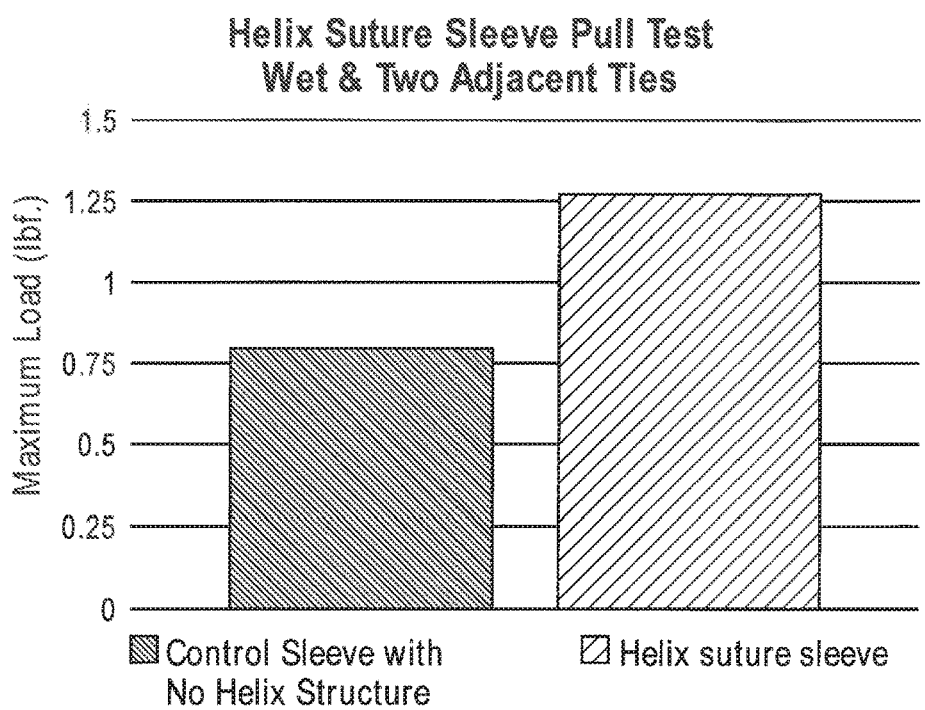
FIG. 8 is a graph depicting comparison wet tied pull test results for a control sleeve having no helix structure and being identical to a suture sleeve used in the industry and the new helical structure equipped suture sleeve depicted in FIGS. 2-6E.

FIG. 8 is a graph depicting comparison wet tied pull test results for a control sleeve having no helix structure and being identical to a suture sleeve used in the industry and the new helical structure equipped suture sleeve 34 depicted in FIGS. 2-6E. The tied wet test is of interest to look at how the suture sleeve will perform in-vivo. As can be understood from FIG. 8, in this worst-case scenario, the new helix suture sleeve design performed one and a half times as well as the non-helix control suture sleeve design.

In use, the suture sleeve 34 is slid on over the lead body 12 distal end 16 and moved proximally along the lead body to a desired anchoring area. Once the lead distal end 16 is implanted as desired, the physician ties a suture over each circumferential recess 62 to fixate the sleeve 34 to the lead body 12. Typically, two to three circumferential recesses 62 may be employed to secure the suture sleeve 34 in place on the lead body 12. The physician then ties a relatively loose suture over the suture sleeve into adjacent tissue to fixate the lead body to the patient. To remove the suture sleeve, the physician cuts the suture ties and either slides the suture sleeve to and over the distal end of the lead body or can cut the suture sleeve in half and peel it away from the lead body.

In manufacturing the helix suture sleeve design of FIGS. 2-6E, the suture sleeve can be made of silicone rubber, silicone rubber-polyurethane-copolymer ("SPC") polyurethane, etc. and can be cast, formed, molded, injection molded, or etc.

In general, while the invention has been described with reference to particular embodiments, modifications can be made thereto without departing from the spirit and scope of the invention. Note also that the term "including" as used herein is intended to be inclusive, i.e. "including but not limited to."

What is claimed is:
1. An implantable therapy lead comprising:
    an elongated lead body having a proximal region and a distal region opposite the proximal region; and
    a suture sleeve supported on the lead body and comprising:
        a proximal end;
        a distal end opposite the proximal end;
        an outer surface extending between the proximal end and distal end;
        an inner surface radially inward of the outer surface and extending between the proximal end and distal end, the inner surface defining a lumen through which the elongated lead body extends; and
        a helical structure helically extending about a longitudinal center axis of the lumen and along the inner surface,
    wherein the suture sleeve is compressible from a first state into a second state by applying a constrictive force to the outer surface of the suture sleeve, and, when in the second state, the helical structure contacts the elongated lead body, at least in part, to resist movement of the elongated lead body relative to the suture sleeve.
2. The lead of claim 1 wherein the helical structure comprises a helical recess defined in the inner surface and projecting radially outward from inner surface.
3. The lead of claim 2, wherein the helical recess comprises a rectangular transverse cross section.
4. The lead of claim 2, wherein the helical recess comprises a recess depth of between approximately 0.008 inches and approximately 0.012 inches relative to the inner surface.
5. The lead of claim 1, wherein the helical structure comprises a helical protrusion projecting radially inward from the inner surface.
6. The lead of claim 5, wherein the helical protrusion comprises a rectangular transverse cross section.
7. The lead of claim 5, wherein the helical protrusion comprises a protrusion height of between approximately 0.008 inches and approximately 0.016 inches relative to the inner surface.
8. The lead of claim 1, wherein the helical structure comprises: a helical recess defined in the inner surface and projecting radially outward from the inner surface; and a helical protrusion projecting radially inward from the inner surface.

9. The lead of claim 8, wherein the helical recess and helical protrusion are helically offset relative to each other.

10. The lead of claim 8, wherein the helical recess and helical protrusion have different transverse widths.

11. The lead of claim 10, wherein the helical recess has a transverse width that is less than a transverse width of the helical protrusion.

12. The lead of claim 1, wherein the inner surface is at least substantially cylindrical.

13. The lead of claim 1, wherein the suture sleeve further comprises a circumferential recess defined in the outer surface and projecting radially inward from the outer surface.

14. The lead of claim 13, wherein the helical structure and the circumferential recess overlap each other along at least one location along a length of the suture sleeve.

15. The lead of claim 1, further comprising a pulse generator configured to electrically couple with the lead.

16. The lead of claim 1, wherein the constrictive force is applied to the outer surface of the suture sleeve by one or more sutures securing the suture sleeve to the elongated lead body.

* * * * *